United States Patent
Ichikawa et al.

(10) Patent No.: US 8,097,763 B2
(45) Date of Patent: Jan. 17, 2012

(54) PROCESS FOR PRODUCTION OF AROMATIC COMPOUND

(75) Inventors: Masaru Ichikawa, Sapporo (JP); Ryoichi Kojima, Sapporo (JP); Yuji Ogawa, Kawagoe (JP); Masamichi Kuramoto, Tokyo (JP)

(73) Assignees: Meidensha Corporation, Tokyo (JP); Masaru Ichikawa, Sapporo-shi (JP)

( * ) Notice: Subject to any disclaimer, the term of this patent is extended or adjusted under 35 U.S.C. 154(b) by 757 days.

(21) Appl. No.: 12/067,148

(22) PCT Filed: Sep. 29, 2006

(86) PCT No.: PCT/JP2006/319497
§ 371 (c)(1),
(2), (4) Date: Mar. 17, 2008

(87) PCT Pub. No.: WO2007/037388
PCT Pub. Date: Apr. 5, 2007

(65) Prior Publication Data
US 2009/0240093 A1    Sep. 24, 2009

(30) Foreign Application Priority Data
Sep. 30, 2005  (JP) ................ 2005-287504

(51) Int. Cl.
*C07C 2/42*  (2006.01)
(52) U.S. Cl. .............. 585/418; 585/419; 585/412
(58) Field of Classification Search ............ 585/418, 585/419, 412
See application file for complete search history.

(56) References Cited

U.S. PATENT DOCUMENTS
4,766,265 A * 8/1988 Desmond et al. ........... 585/415

FOREIGN PATENT DOCUMENTS
JP  10-272366 A  10/1998
JP  11-060514 A  3/1999
JP  2005-255605 A  9/2005

OTHER PUBLICATIONS

S. Wong et al., "Methane and ethane activation without adding oxygen: promotional effect of W in MO-W/HZSM-5," Catalysis Letters, 38, 1996, pp. 39-43.
F. Solymosi et al., "Conversion of ethane in benzene on Re/ZSM-5," Catalysis Letters, vol. 98, Nos. 1-2, 2004, pp. 7-11.
F. Solymosi et al., "Conversion of ethane into benzene on $Mo_2C$/ZSM-5 catalyst," Applied Catalysis A: General, 166, 1998, pp. 225-235.
J. Hui et al., "Non-oxidizing aromatization of methane and ethane over supported Mo catalysts," Journal of Molecular Catalysis, vol. 12, No. 5, 1998, p. s335-341.
W. Chu et al., "Dehydroaromatization of Methane with a Small Amount of Ethane for higher Yield of Benzene," Chinese Chemical Letters, vol. 15, No. 5, 2004, pp. 591-593.
Amin et al., "Characterization and Activity of Cr, Cu and Ga Modified ZSM-5 for Direct Conversion of Methane to Liquid Hydrocarbons," Journal of Natural Gas Chemistry 12(2003): 123-134.

* cited by examiner

*Primary Examiner* — Thuan Dinh Dang
(74) *Attorney, Agent, or Firm* — Foley & Lardner LLP

(57) ABSTRACT

An aromatic compound, particularly benzene, is stably produced in the presence of a catalyst from a lower hydrocarbon having 2 or more carbon atoms, particularly from an ethane-containing gas composition such as ethane gas and natural gas. Disclosed is a process for producing an aromatic compound by reacting ethane or an ethane-containing raw gas in the presence of a catalyst. The catalyst may comprise molybdenum carried on metallosilicate such as H-type ZSM-5H or H-type MCM-22. In the reaction, the temperature is from 550 to 750° C., preferably not lower than 600° C. and not higher than 680° C. Additionally, the raw gas further contains methane and hydrogen is added thereto, thereby improving the production efficiency and stability.

10 Claims, 4 Drawing Sheets

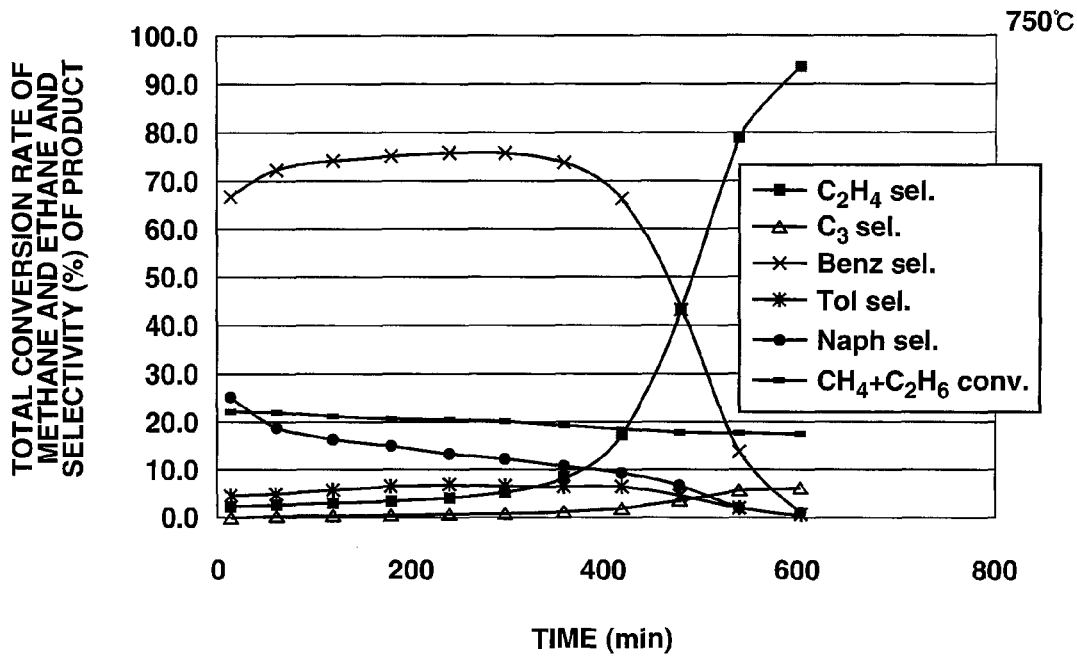
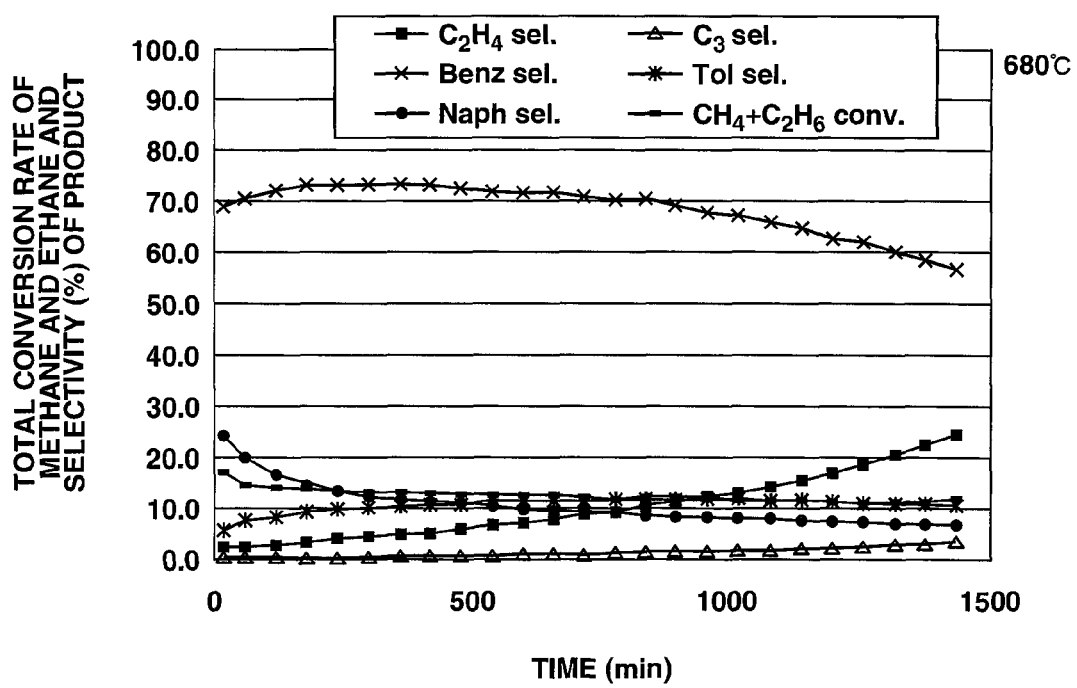

PROCESS FOR PRODUCTION OF AROMATIC COMPOUND

TECHNICAL FIELD

The present invention relates to a process for stably producing an aromatic compound such as benzene, toluene and naphthalene (particularly, benzene) in the presence of a catalyst. The aromatic compound is produced from a lower hydrocarbon having 2 or more carbon atoms, particularly from an ethane-containing gas composition such as an ethane gas, natural gas and a reformed gas containing a lower hydrocarbon having 2 or more carbon atoms. The reformed gas is obtained by a hydrogen reforming reaction such as Fisher-Tropsch (FT) reaction of a coal gas, a coke oven gas or the like.

BACKGROUND ART

Natural gas is expected to be an effective energy against global warming, and therefore an interest in techniques using natural gas has grown. Typically, natural gas contains ethane ($C_2H_6$) in an amount ranging from 1 to 10%, propane ($C_3H_8$) in an amount less than 5%, butane ($C_4H_{10}$) in an amount less than 2%, pentane ($C_5H_{12}$) in an amount less than 1% and hexane ($C_6H_{14}$) in an amount less than 0.5%, other than methane ($CH_4$) contained in an amount ranging from 70 to 98% as a main component.

In the use of natural gas, methane gas serving as the main component is held in high regard so that ethane contained in the natural gas is sometimes eliminated when the natural gas is put into storage in liquefied form or when the natural gas is transported through a pipeline or the like.

In Europe and the United States, ethane is generally known as a raw material for ethylene production in petrochemical industry; however, in Again nations including Japan, a raw material for ethylene is naphtha and therefore ethane is treated as a redundant gas so as not to be recognized to be important.

One of prior arts of producing benzene from lower hydrocarbons is disclosed in patent literature 1 (Japanese Patent Provisional Publication No. 2005-255605), in which a main lower hydrocarbon is methane and the other usable lower hydrocarbons are exemplified by ethane, ethylene, propylene, n-butane, isobutene, n-butene and isobutene. Patent literature 1 is to provide an art widely applicable to lower hydrocarbons, and not to focus on ethane for studying the effective use of ethane.

As discussed above, ethane is still treated as a redundant gas and is not yet effectively used, even though it exists as a reformed gas (a raw gas) which is not yet used in a gasification process for a lignitious coal or the like, the process being seen in steelmaking industry. Therefore, it is a vital object to develop an art of achieving the effective use of ethane.

Patent literature 1: Japanese Patent Provisional Publication No. 2005-255605

DISCLOSURE OF THE INVENTION

The present invention is made in view of the above-mentioned circumstance, and an object of the present invention is to achieve the effective use of ethane by providing a process for stably producing an aromatic compound such as benzene, toluene and naphthalene from an ethane-containing gas composition such as an ethane gas, natural gas and a reformed gas containing a lower hydrocarbon having 2 or more carbon atoms, the reformed gas being obtained by a hydrogen reforming reaction such as Fisher-Tropsch (FT) reaction of a coal gas, a coke oven gas or the like.

An invention as claimed in Claim 1 is a process for producing an aromatic compound by reacting ethane or an ethane-containing raw gas in presence of a catalyst, wherein the catalyst is formed such that metallosilicate carries one of molybdenum, rhenium and tungsten, and one of rhodium and platinum as a secondary metal in addition to molybdenum, rhenium and tungsten.

An invention as claimed in Claim 2 is a process for producing an aromatic compound as claimed in Claim 1, wherein a reaction temperature applied in a reaction made in the presence of the catalyst is from 550 to less than 750° C., preferably not less than 600° C. and not more than 680° C.

An invention as claimed in Claim 3 is a process for producing an aromatic compound as claimed in Claim 1, wherein the metallosilicate is formed of H-type ZSM-5 or H-type MCM-22.

An invention as claimed in Claim 4 is a process for producing an aromatic compound as claimed in Claim 1, wherein hydrogen is added to the raw gas in an amount more than 2% and less than 10%, preferably in an amount ranging from 4 to 8%.

An invention as claimed in Claim 5 is a process for producing an aromatic compound by reacting an ethane-containing raw gas in presence of a catalyst, the process comprising the steps of: a first stage for reforming ethane contained in the raw gas by the process for producing an aromatic compound, the process as claimed in Claim 1; and a second stage for reacting a gas produced at the first stage in presence of a catalyst again, wherein the catalyst used in the second stage is formed carrying molybdenum and a platinum-group element.

An invention as claimed in Claim 6 is a process for producing an aromatic compound as claimed in Claim 5, wherein the platinum-group element contained in the catalyst is rhodium, ruthenium, iridium, palladium or platinum.

An invention as claimed in Claim 7 is a process for producing an aromatic compound, as claimed in Claim 5, wherein hydrogen is added to the gas produced at the first stage in a reaction made by the second stage, in an amount more than 2% and less than 10%, preferably in an amount ranging from 4 to 8%.

An invention as claimed in Claim 8 is a process for producing an aromatic compound by reacting an ethane-containing raw gas in presence of a catalyst, wherein an outlet gas that has underwent the reaction made in the second stage of the process for producing an aromatic compound as claimed in Claim 5 is supplied to the first stage again, thereby being circulated between the first stage and the second stage twice or more to be reacted.

According to the inventions as claimed in Claims 1 to 4, an aromatic compound can be stably produced from raw materials such as the ethane-containing gas including ethane gas, natural gas and the like.

According to the inventions as claimed in Claims 5 to 7, the raw gas is reacted in the presence of a Mo/HZSM-5 catalyst in the first stage so as to convert ethane into benzene, and thereafter in the second stage a technique for producing benzene from methane is applied to a gas produced in the first stage. With this, natural gas is supplied as it is without undergoing separation and purification, which allows natural gas to directly convert into benzene. Particularly in a natural gas-producing region or in an environment where natural gas is supplied through a pipeline or the like, this technique is certainly to be an extremely effective one.

According to the invention as claimed in Claim 8, an outlet gas that has underwent the reaction made in the second stage is supplied to the first stage again and circulated between the first stage and the second stage twice or more to be reacted. With this, ethane gas produced in the second stage (in an amount ranging from 10 to 20%) can be reacted in the first stage, which enhances a use efficiency of the raw gas further.

BRIEF DESCRIPTION OF DRAWINGS

FIG. 3 is a plot of properties, showing a time variation in a selectivity (%) of product (ethylene, propylene, benzene, toluene, and naphthalene) at a reaction temperature of 750° C.

FIG. 4 is a plot of properties, showing a time variation in a selectivity (%) of product (ethylene, propylene, benzene, toluene, and naphthalene) at a reaction temperature of 680° C.

BEST MODE FOR CARRYING OUT THE INVENTION

Figure 1:
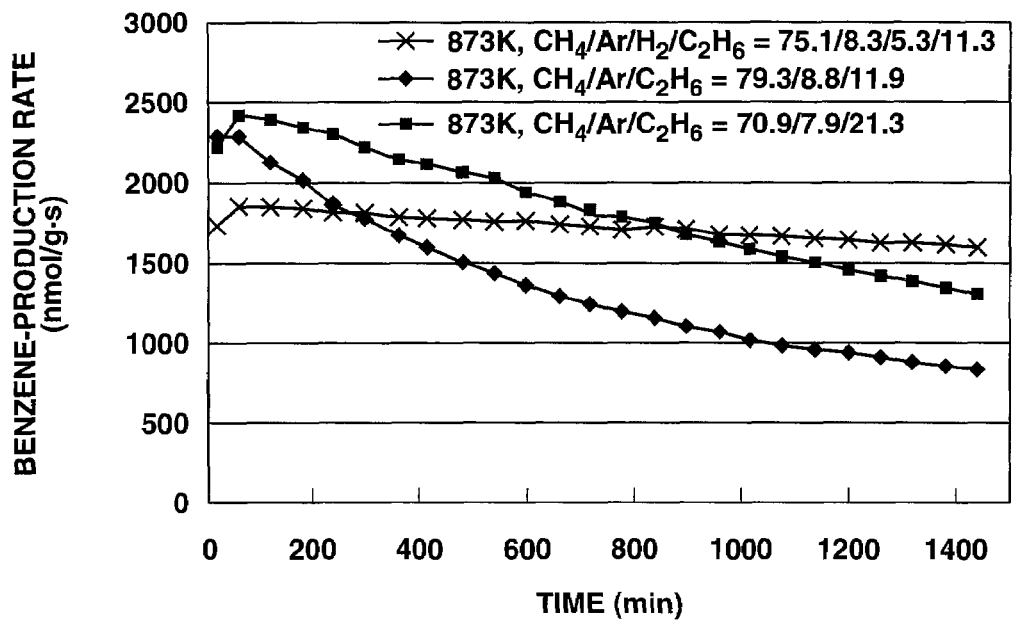
FIG. 1 is a plot of properties, showing a time variation in a benzene-production rate in the case where each of gas samples 1 to 3 was supplied to and reacted with a Mo/HZSM-5 catalyst.

The inventors have studied a technique for producing an aromatic compound (mainly benzene) and hydrogen from a lower hydrocarbon (mainly methane) by adopting a catalytic and chemical conversion technique, with which they have hitherto obtained various results.

Hence, they conducted various experiments based on the thus cultivated catalytic and chemical conversion technique, for a purpose of producing an aromatic compound from an ethane-containing gas composition such as ethane gas and natural gas while maintaining a stable production rate.

1. Production of Catalyst

As a catalyst, a H-type ZSM-5 zeolite catalyst is employed, the catalyst carrying molybdenum thereon so as to be referred to as "Mo/HZSM-5 catalyst" hereinafter.

(1) Carrying Molybdenum

First of all, 522 g of ammonium heptamolybdate hexahydrate (containing 300 g of molybdenum) was dissolved in 5 liters of distilled water, thereby preparing an impregnation solution. Then, 5 kg of the zeolite was added to the thus prepared impregnation solution and stirred for 3 hours by a high-speed agitator. Further, the stirred substance was dried, i.e., evaporated until solidified, at 70 to 100° C. Thereafter, the dried substance was calcined in air at 550° C. for 5 hours, thereby obtaining zeolite powder which carries molybdenum in an amount of 15% by weight relative to zeolite.

(2) Preparation of Catalyst Components

Composition of an inorganic component: molybdenum-carrying zeolite (82.5 wt. %), clay (10.5 wt. %), and glass fiber (7 wt. %)

Total composition: the above-mentioned inorganic component (65.4 wt. %), an organic binder (13.6 wt. %), polymeric beads (which was available from Matsumoto Yushi-Seiyaku Co., Ltd. under the trade name of F-80E, and had an average diameter of 90 to 110 μm and a true specific gravity of 0.0025) (5.0 wt. %), and a water content (21 wt. %)

(3) Shaping Catalyst

The inorganic component, the organic binder, polymeric beads and the water content prepared in the above-mentioned ratio were mixed or kneaded by a means of kneading (a kneader). Subsequently, the thus mixed substance was shaped by a vacuum extrusion machine into a rod (5 mm in diameter). An extrusion pressure applied during this shaping process was set within a range of from 70 to 100 $kg/cm^2$.

(4) Drying and Calcination of Catalyst

A drying process was carried out at 100° C. for about 5 hours, so as to eliminate the water content added in the shaping process. Temperature-increasing and temperature-decreasing rates in a calcination process were set within a range of from 30 to 50° C./hour. During the calcination process, the temperature was kept within a range of from 120 to 150° C. for 2 hours in order not to instantaneously calcine the polymeric beads added in the shaping process. Thereafter, there was carried out twice such a process as to keep temperature within a range of from 250 to 450° C. for 2 to 5 hours in order not to instantaneously calcine the organic binder, thereby removing the binder. When the temperature-increasing and temperature-decreasing rates exceed the above-mentioned rate and when a temperature-keeping time is not ensured, the binder calcines instantaneously so as to decrease the strength of the calcined substance.

(5) Carbonizing Treatment

The catalyst produced by the above-mentioned method was increased in temperature to 550° C. in an air atmosphere and then kept in this condition for 1 hour. Thereafter, the catalyst was increased in temperature to 700° C. upon replacing the atmosphere with that of a reaction gas ($CH_4+4H_2$), and kept under this condition for 1 hour.

2. Preparation of Gas Samples

Then, there were prepared three kinds of gases each of which simulates natural gas by containing methane and ethane as follows.

Composition of gas sample 1: methane (75.1%), argon (8.3%), hydrogen (5.3%), and ethane (11.3%)

Composition of gas sample 2: methane (79.3%), argon (8.8%), and ethane (11.9%)

Composition of gas sample 3: methane (70.9%), argon (7.9%), and ethane (21.3%)

3. Basic Experiment

The Mo/HZSM-5 catalyst was charged into a reaction pipe of a fixed-bed flow reactor (the pipe had an internal diameter of 18 mm and was produced in such a manner as to make a calorizing treatment on a Inconel 800H's portion with which gas is to be brought into contact), to which the gas samples 1 to 3 were supplied. Then, the catalyst was reacted with each gas sample under the following conditions:

Space velocity of reaction=450 ml/g–*MFI/h* (a space velocity that $C_2H_6$ had in the reaction gas), Reaction temperature: 600° C. (873 K),
Reaction time: 1400 minutes, and
Reaction pressure: 0.3 MPa.

During the reaction, a product analysis was conducted while a time variation in an aromatic compound-production rate (benzene-production rate) was examined. The product analysis was conducted by using TCD-GC and FID-GC.

Results of Experiment 1 are shown in FIG. 1. It is found from the results shown in FIG. 1 that a benzene production was made. Additionally, it is found to be preferable for stability of a benzene-production rate that hydrogen is contained in the gas sample.

4. Applied Experiment 1

An experiment in which a temperature condition is further changed was conducted by using the gas sample 1 with which the stability of the benzence-production rate was confirmed in the basic experiment In this experiment, the Mo/HZSM-5 catalyst was charged into a reaction pipe of a fixed-bed flow reactor (the pipe had an internal diameter of 18 mm and was produced in such a manner as to make a calorizing treatment on a Inconel 800H's portion with which gas is to be brought into contact). Then, the catalyst was reacted with the gas sample 1 under the following conditions:

Space velocity of reaction=450 ml/g-*MFI/h* (a space velocity that $C_2H_6$ had in the reaction gas), Reaction time: 1400 minutes,
Reaction pressure: 0.3 MPa, and
Temperature condition changed as follows: 750° C. (1023 K), 680° C. (953 K), 600° C. (873 K), and 550° C. (823 K)

During the reaction, a product analysis was conducted while a time variation in a rate at which each of products such as ethylene, propylene, benzene, toluene and naphthalene is produced was examined. The product analysis was conducted by using TCD-GC and FID-GC.

Results of the applied experiment are shown in FIGS. 2 to 6.

Figure 2:
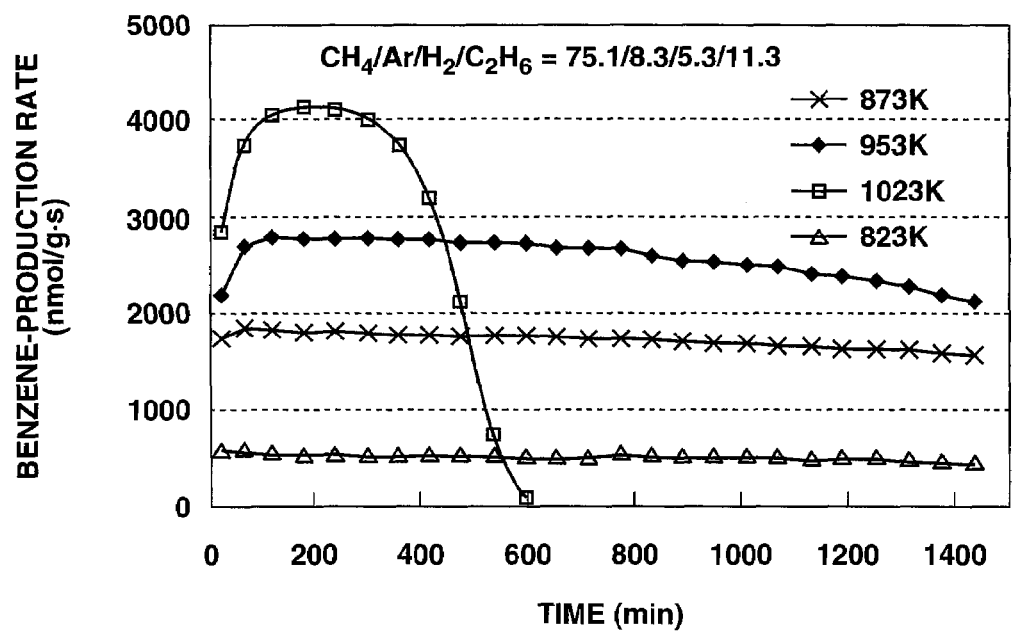
FIG. 2 is a plot of properties, showing a time variation in a benzene-production rate at each reaction temperature.
Figure 5:
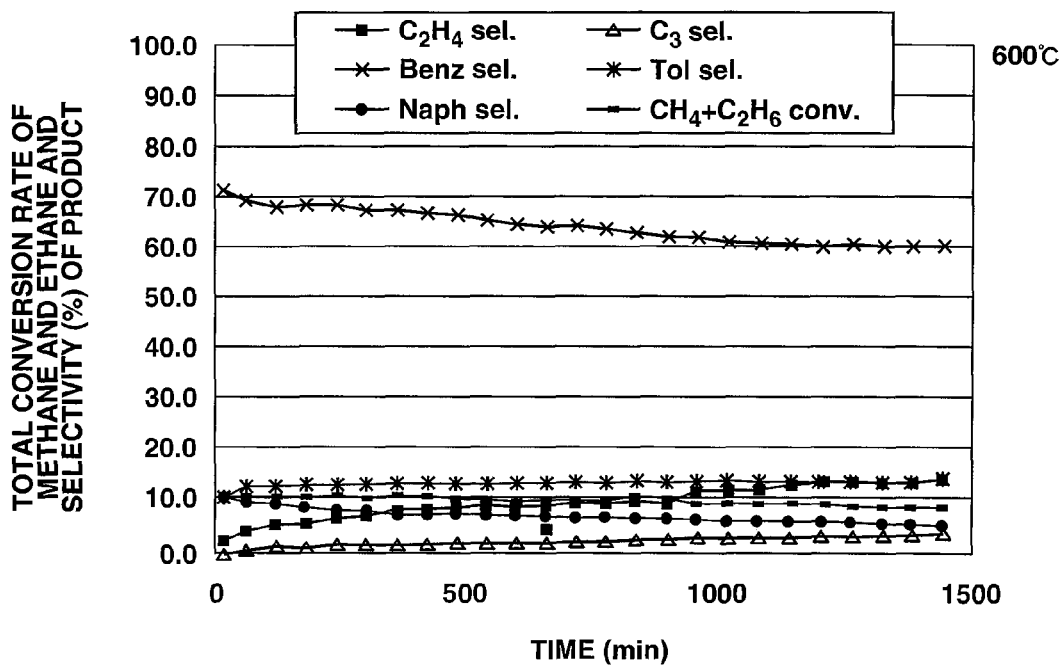
FIG. 5 is a plot of properties, showing a time variation in a selectivity (%) of product (ethylene, propylene, benzene, toluene, and naphthalene) at a reaction temperature of 600° C.
Figure 6:
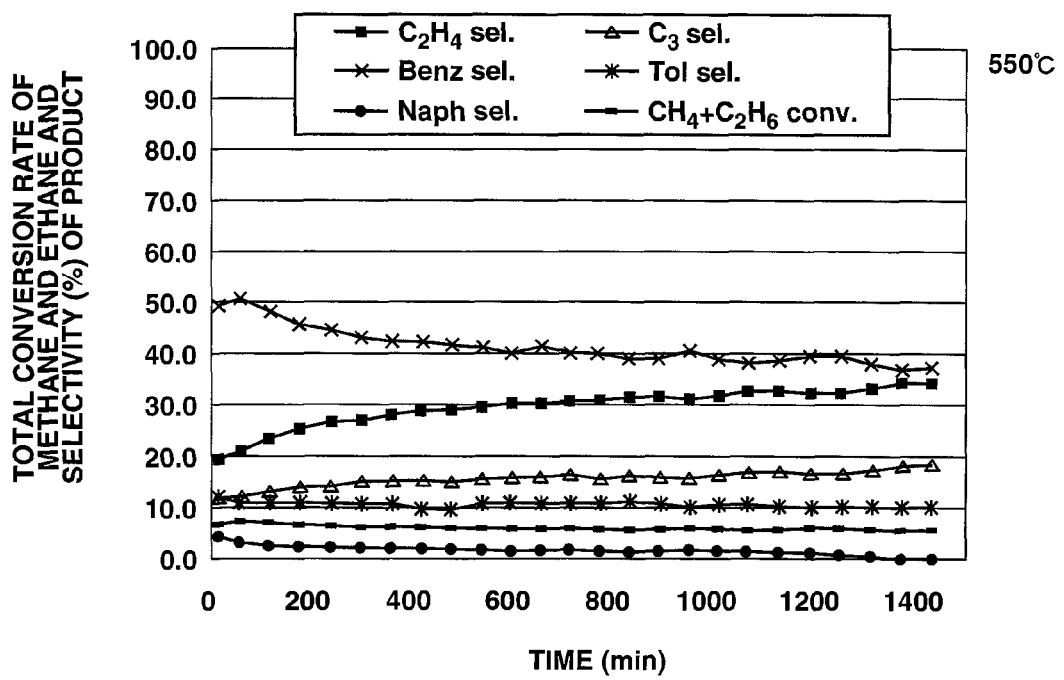
FIG. 6 is a plot of properties, showing a time variation in a selectivity (%) of product (ethylene, propylene, benzene, toluene, and naphthalene) at a reaction temperature of 550° C.

FIG. 2 is a graph showing a time variation in a benzene-production rate at each reaction temperature. It is found from the results shown in FIG. 2 that benzene is stably produced while maintaining a certain production rate, at each of the reaction temperatures of 680° C. and 600° C. At a reaction temperature of 750° C., a benzene-production rate is high during the early stages or of reaction (up to 400 minutes); however, the production rate thereafter drops significantly, and results in a value of 0 after 600 minutes. At a reaction temperature of 550° C., a production rate is extremely low, though it is stable.

Additionally, FIGS. 3 to 6 show results obtained by examining a time variation in a selectivity (%) of product (ethylene, propylene, benzene, toluene and naphthalene) at each reaction temperature of 750° C., 680° C., 600° C. and 550° C. In FIGS. 3 to 6, "$C_2H_4$ sel." represents a selectivity of $C_2H_4$. "$C_3$ sel." represents a selectivity of a $C_3$ compound. "Benz sel." represents a selectivity of benzene. "Tol sel." represents a selectivity of toluene. "Noph sel." represents a selectivity of naphthalene. "$CH_4$ +$C_2H_6$ conv." represents a total conversion rate of methane and ethane.

5. Verification of Results of Applied Experiment 1 (Confirmation of Benzene Production Derived from Ethane)

In order to confirm that benzene is produced from ethane reacted in this experiment, there was conducted an analysis of the above-mentioned experimental results.

Table 1 provides a summary of a total conversion rate and a percentage of each product (ethylene, propylene, benzene, toluene and naphthalene), which are obtained at each reaction temperature of 750° C., 680° C., 600° C. and 550° C.

TABLE 1

| Reaction Temperature (° C.) | Total conversion rate (%) based on carbon | Selectivity of product (%, based on carbon) | | | | |
|---|---|---|---|---|---|---|
| | | Ethylene | Propylene | Benzene | Toluene | Naphthalene |
| 550 | 7.4 | 23.8 | 13.7 | 48.3 | 11.5 | 2.7 |
| 600 | 10.8 | 5.3 | 1.1 | 68.4 | 12.7 | 9.1 |
| 680 | 13.9 | 2.8 | 0.1 | 74.1 | 5.7 | 16.0 |
| 750 | 20.8 | 2.5 | 0.2 | 72.0 | 8.6 | 16.7 |

Table 2 shows an average conversion rate (a theoretical value) of methane into benzene, at each reaction temperature at which the experiment was conducted.

TABLE 2

| Average conversion rate (%) of methane | | | |
|---|---|---|---|
| 550° C. | 600° C. | 680° C. | 750° C. |
| 0.00355 | 0.2892 | 3.34 | 7.98 |

In comparison of a theoretical conversion rate as shown in Table 2 and a total conversion rate shown in Table 1 as experimental results, it is found that the total conversion rates obtained as the experimental result are much more than a conversion rate of methane alone, in any of 750° C., 680° C. and 600° C. It is clearly verified from these results that a component which is contained in the gas sample 1 but other than methane, i.e. ethane, is reacted to be converted into benzene.

With the above-mentioned results, it is confirmed that: benzene can be produced directly from ethane when an ethane-containing gas composition is used as a raw gas and the raw gas is reacted in the presence of the Mo/HZSM-5 catalyst according to the present invention; hydrogen is preferably added to the raw gas in order to maintain a stable production rate; and a reaction temperature is within a range of from 550 to less than 750° C., preferably not less than 600° C. and not more than 680° C. thereby stably producing benzene while maintaining a certain production rate.

With a result of researches that the inventors have hitherto carried out, a reaction temperature of 750° C. in such a reaction as to produce benzene from methane has been known to be a temperature condition providing an extremely preferable result. However, it is found from the present experiments, that a temperature preferable to the benzene production is within a range further low and clearly different from that preferable for producing benzene from methane. This is a factor verifying that benzene is produced by reaction of a component other than methane, i.e. reaction of ethane, in the present experiment.

6. Applied Experiment 2 (Confirmation that Benzene is Produced from Ethane, and Effects of Methane and Hydrogen)

In order to confirm results of verification of the applied experiment 1 in which ethane is reacted to be converted into benzene, and in order to confirm effects of methane contained in the gas samples 1 to 3 and of added hydrogen, four kinds of gas samples, i.e. gas samples 4 to 7 were prepared.

Composition of gas sample 4: helium (87.0%), argon (11.7%) and ethane (1.3%)

Composition of gas sample 5: methane (79.3%), argon (8.8%) and ethane (11.9%)

Composition of gas sample 6: helium (84.0%), argon (1.1%), hydrogen (5.4%) and ethane (9.1%)

Composition of gas sample 7: methane (75.2%), argon (8.4%), hydrogen (5.3%) and ethane (11.3%)

A reaction experiment was conducted by using these gas samples 4 to 7. In this reaction experiment, the Mo/HZSM-5 catalyst was charged into a reaction pipe of a fixed-bed flow reactor (the pipe had an internal diameter of 18 mm and was produced in such a manner as to make a calorizing treatment on a Inconel 800H's portion with which gas is to be brought into contact), and the conditions were as follows:

Space velocity of reaction=450 ml/g–$MFI/h$ (a space velocity that $C_2H_6$ had in the reaction gas), Reaction time: 1400 minutes,
Reaction pressure: 0.3 MPa, and
Reaction temperature: 600° C. at which a good result was obtained in both the basic experiment and the applied experiment 1.

Figure 7:
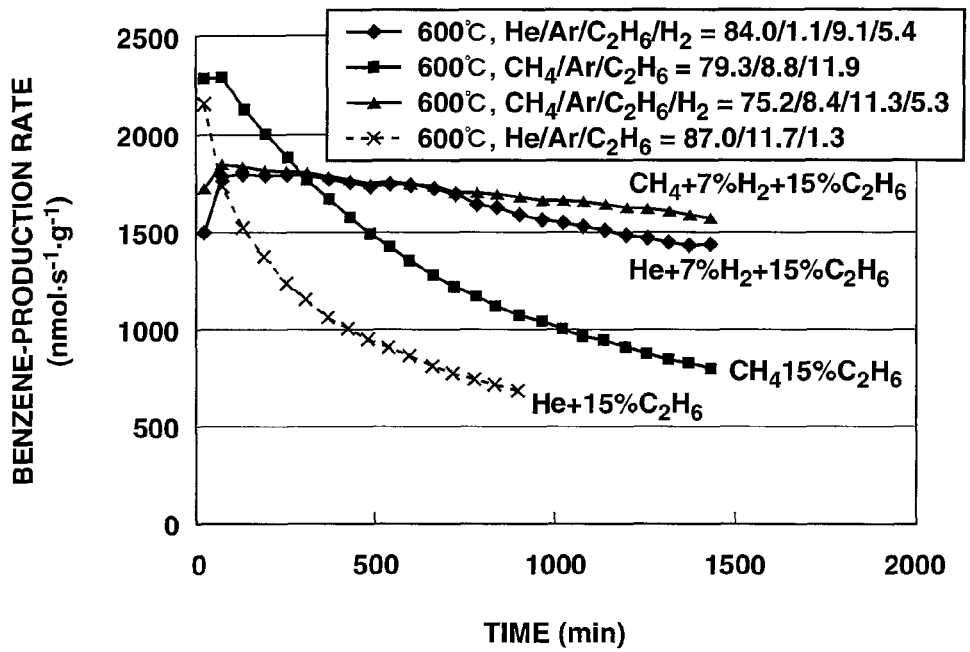
FIG. 7 is a plot of properties, showing a time variation in a benzene-production rate in the case where each of gas samples 4 to 7 was supplied to and reacted with a Mo/HZSM-5 catalyst.

Then, the experiment was carried out by examining a time variation in a benzene-production rate. As a product analysis, TCD-GC and FID-GC were used. Results of the applied experiment 2 are shown in FIG. 7.

A result of the reaction experiment using the gas sample 4 shows that benzene is produced, with which it is verified that ethane is directly reacted thereby producing benzene.

A result of the reaction experiment using the gas sample 5 shows that a benzene-production rate is improved when methane is contained in the raw gas, as compared with the case of ethane alone (the gas sample 4). With this, it is supposed that methane is activated in the coexistence of methane so that a part thereof is converted into ethane to be reacted.

Further, a result of the reaction experiment using the gas sample 6 shows that a rate at which benzene is produced from ethane is largely improved in stability when hydrogen is contained in the raw gas. With this, the effect of addition of hydrogen is verified, the effect being confirmed by the basic experiment.

Furthermore, a result of the reaction experiment using the gas sample 7 shows that a rate at which benzene is produced from ethane is more improved in stability than that in the case where hydrogen alone is added, when methane and hydrogen are contained in the raw gas.

With the results of the applied experiment 2, it is verified that ethane is reacted directly thereby producing benzene. In addition to this, it is confirmed that: a benzene-production rate is improved in the coexistence of methane in the raw gas; a benzene-production rate is largely improved in stability when hydrogen is added to the raw gas; and methane and hydrogen are contained in the raw gas so that a rate at which benzene is produced from ethane is more improved in stability than that in the case where hydrogen alone is added. Further, effects to be brought about when methane and hydrogen are contained in the raw gas are confirmed also.

7. Applied Experiment 3 (Performance of Secondary Metal-carrying Catalyst)

Then, a catalyst which carries a secondary metal in addition to molybdenum (the catalyst is hereinafter referred to as "a secondary metal-carrying catalyst") was produced, and there was conducted an experiment for verifying a difference in performance between the secondary metal-carrying catalyst and the hitherto used Mo/HZSM-5 catalyst.

Production of Secondary Metal-carrying Catalyst 1

A secondary metal-carrying catalyst 1 was prepared such that molybdenum and rhodium were carried on H-type ZSM-5. The secondary metal-carrying catalyst 1 was produced by the same method as the production method of Mo/HZSM-5, discussed in "1. Production of catalyst", with the exception of a step of carrying. In the step of carrying, there was used ammonium molybdate to which rhodium chloride was added. Molybdenum was carried in an amount of 6% by weight relative to the weight of a sintered substance. Rhodium was carried at a mole ratio to molybdenum, more specifically at the following ratio:

Rhodium: molybdenum=0.2:1.

Production of Secondary Metal-carrying Catalyst 2

A secondary metal-carrying catalyst 2 was produced such that the H-type ZSM-5 zeolite catalyst carries molybdenum and platinum thereon, by the following method.

(1) Carrying Molybdenum and Platinum-group Component 522 g of ammonium heptamolybdate hexahydrate (containing 300 g of molybdenum) and 305 g of 40 wt. % platinum-containing chloroplatinate hydrate (containing 122 g of platinum) were mixed and dissolved in 5 liters of distilled water, thereby preparing an impregnation solution. Then, 5 kg of the zeolite was added to the thus prepared impregnation solution and stirred for 3 hours. Upon drying the stirred substance to eliminate the water content, the substance was calcined in air at 550° C. for 10 hours, thereby obtaining metal-carrying zeolite powder which carries molybdenum and platinum. The metal-carrying zeolite powder carries molybdenum in an amount of 6 wt. % relative to the zeolite. Platinum was carried at a mole ratio to molybdenum, more specifically at the following ratio:

Platinum: molybdenum=0.2:1.0

(2) Preparation of Catalyst Composition

A catalyst composition and a composition ratio thereof are as below.

Inorganic component:organic component:polymeric beads:water content=65.4:13.6:5.0:21.0

Further, a composition of the inorganic component and a composition ratio thereof are as below.

Metal-carrying zeolite:clay:glass fiber=82.5:10.5:7.0

The inorganic component, the organic component and the water content were mixed in the above-discussed ratio, and then kneaded by a means of kneading, for example, by a kneader. Subsequently, the thus mixed substance was shaped by a vacuum extrusion machine into a rod (5 mm in diameter). An extrusion pressure applied during this process was set within a range of from 70 to 100 kg/cm$^2$. Then, the rod-like substrate having a diameter of 5 mm, obtained by the extrusion, was cut to be 10 mm thereby obtaining an extrudate.

(4) Drying and Calcination of Catalyst

A drying process was carried out at 100° C. for about 12 hours in order to eliminate the water content added in the shaping process. Temperature in a calcination process was set within a range of from 600 to 700° C. Temperature-increasing and temperature-decreasing rates in the calcination process were set within a range of from 30 to 50° C. During the calcination process, the temperature was kept within a range of from 120 to 150° C. for 2 hours in order not to instantaneously calcine the added polymeric beads. Thereafter, there was carried out twice a process for keeping temperature within a range of from 250 to 450° C. for about 2 to 5 hours in order not to instantaneously calcine the organic binder, thereby removing the binder. When the temperature-increasing and temperature-decreasing rates exceed the above-mentioned rate and when a temperature-keeping time is not enough to remove the binder, the binder is to calcine instantaneously to decrease the strength of the calcined substance. With the above operation, a foam catalyst carrying molybdenum and a platinum-group component was obtained.

(5) Carbonizing Treatment

The catalyst produced by the above-mentioned method was increased in temperature to 550° C. in an air atmosphere and then kept in this condition for 1 hour. Thereafter, the catalyst was increased in temperature to 700° C. upon replacing the atmosphere with that of a reaction gas ($CH_4+4H_2$), and kept under this condition for 1 hour.

Reaction Experiment

A reaction experiment with ethane was conducted by using the secondary metal-carrying catalysts 1 and 2 produced through the above-mentioned production process, as well as the Mo/HZSM-5 catalyst In this experiment, each catalyst was charged into a reaction pipe of a fixed-bed flow reactor (the pipe had an internal diameter of 18 mm and was produced in such a manner as to make a calorizing treatment on a Inconel 800H's portion with which gas is to be brought into contact), in an amount of 7 g. The conditions were as follows:

Space velocity of reaction=450 ml/g-*MFI*/h (a space velocity that $C_2H_6$ had in the reaction gas), Space velocity of reaction=3000 ml/g-*MFI*/h (a space velocity that $CH_4$ had in the reaction gas), Reaction time: 1400 minutes, and Reaction pressure: 0.3 MPa.

A temperature condition was set at 680° C. at which a good result was obtained in both the basic experiment and the applied experiment 1. Then, and a conversion amount of methane and ethane was measured with time by using TCD-GC and FID-GC. Results of the applied experiment 3 are shown in FIG. 8

Figure 8:
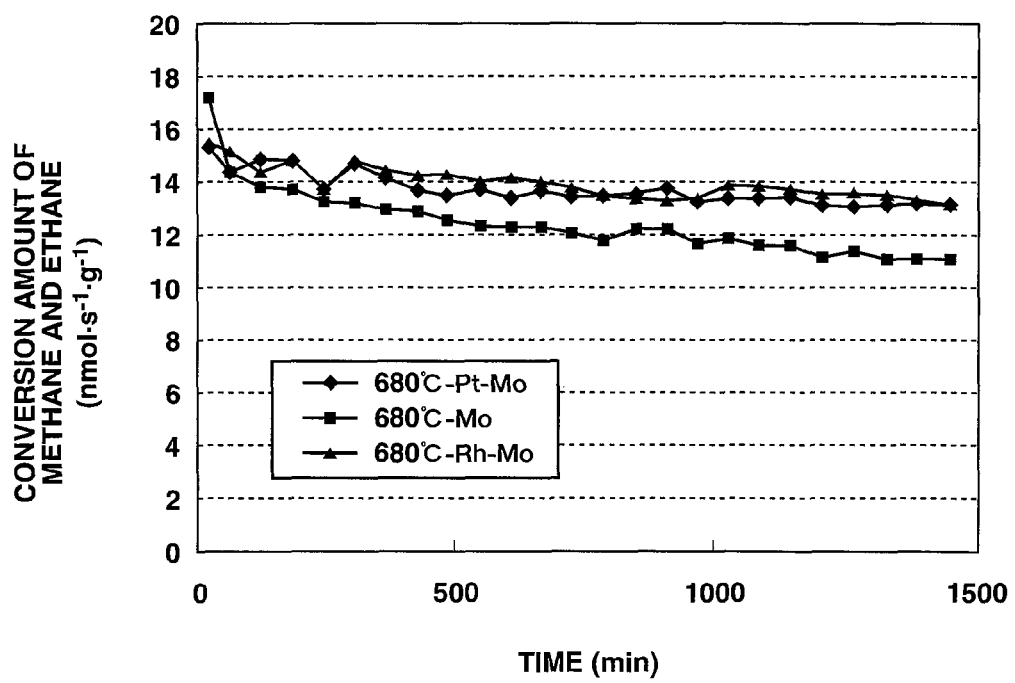
FIG. 8 is a plot of properties, showing a time variation in a conversion amount of methane and ethane in the cases of using as a catalyst: a Mo/HZSM-5 catalyst (680° C.-Mo); secondary metal-carrying catalyst 1 (680° C.-Rh—Mo) which carries rhodium in addition to molybdenum, as a secondary metal; and secondary metal-carrying catalyst 2 (680° C.-Pt—Mo) which carries platinum in addition to molybdenum, as a secondary metal.

From the results as shown in FIG. 8, it is found that both the secondary metal carrying catalyst 1 (represented in FIG. 8 as 680° C.-Rh—Mo) which carries rhodium in addition to molybdenum as the secondary metal and the secondary metal carrying catalyst 2 (represented in FIG. 8 as 680° C.-Pt—Mo) which carries platinum in addition to molybdenum as the secondary metal are improved in conversion amount, as compared with the Mo/HZSM-5 catalyst (represented in FIG. 8 as 680° C.-Mo) which carries molybdenum alone. With this, carrying the secondary metal is found to be effective.

Rhenium or tungsten may be effectively used instead of molybdenum. Therefore, in addition to each of the catalysts used in the above-mentioned experiment, a catalyst which carries rhodium or platinum as the secondary metal may be used.

When aluminosilicate serves as metallosilicate, it may be a porous material formed of silica and alumina and formed with pores of 4.5 to 6.5 angstrom in diameter. Examples of effective metallosilicate include those of MCM such as MCM-22, molecular sieve 5A, and faujasite (of type NaY or NaX), in addition to ZSM represented by the above-mentioned ZSM-5. Effective examples further include: porous materials (such as ALPO-5 and VPI-5) formed with micropores of 6 to 13 angstrom in diameter and containing phosphoric acid as a main component; a zeolite substrate formed with a channels; and those who contains silica as a main component and alumina as a part and is formed with cylindrical mesopores (or channel) of 10 to 1000 angstrom in diameter, such as FSM-16 and MCM-41. Further, metallosilicate is further exemplified by those made of silica and titania, in addition to the above-mentioned aluminosilicate.

8. Application of Experimental Results (Hybridization)

Each experimental result as discussed above shows not only that benzene is produced directly from ethane to allow an effective use but also that this brings further advantages when combined with the results of the technique the inventors have hitherto studied for producing benzene directly from methane as discussed above.

The technique the inventors have hitherto studied will be discussed hereinafter. As a process for producing an aromatic compound such as benzene and hydrogen from a lower hydrocarbon (especially methane), a process in which methane is reacted in the presence of catalyst and in the absence of oxygen and oxidizing agent is known. Based on a catalyst formed such that a porous metallosilicate carries molybdenum (for example, Japanese Patent Provisional Publication No. 10-272366), another catalyst is developed by adding a metal other than molybdenum as a secondary component (for example, Japanese Patent Provisional Publication No. 11-60514), thereby allowing improvements in catalytic property. With studies further diligently made for the purpose of stabilizing catalytic activity over a long period of time and of improving selectivity, a measure of success was obtained and a patent application was already filed, in which the catalytic activity was so recovered as to achieve stability over a long period of time: when platinum-group metal (such as platinum, rhodium, ruthenium, iridium, palladium and the like) is carried in addition to molybdenum as the secondary metal component; when hydrogen gas is added to a raw gas which is to be reacted to the catalyst (in an amount more than 2% and less than 10%, preferably in an amount ranging from 4 to 8%); and when the supply of the raw gas is cut off for a certain period of time while maintaining the supply of the hydrogen gas.

In the case where the raw gas is a gas containing ethane in addition to methane serving as a main component, ethane contained in the raw gas is firstly converted into benzene in the first stage (prereformer) by reacting the raw gas in the presence of such a catalyst as to produce benzene from ethane, the catalyst being confirmed by the above experiments to be effective. Thereafter, in the second stage, the inventors' technique for producing benzene from methane is applied to a gas produced in the first stage. With this, natural gas is supplied as it is without undergoing separation and purification, which allows natural gas to directly convert into benzene. Particularly in a natural gas-producing region or in an environment where natural gas is supplied through a pipeline or the like, this technique is certainly to be an extremely effective one.

Further, ethane is produced in an amount ranging from 10 to 20% in the second stage so as to be an exhaust gas in the second stage. Therefore, when an outlet gas in the second stage is supplied to the first stage again, more specifically when the outlet gas is circulated twice or more to be reacted, a use efficiency of the raw gas can be further enhanced.

Though the catalyst can be suitably selected from the above-mentioned kinds of catalysts, the Mo/HZSM-5 catalyst whose raw materials are obtained at a low cost is preferably used in the case where the first stage serves as the prereformer.

The invention claimed is:

1. A process for producing an aromatic compound by reacting ethane or an ethane-containing raw gas in presence of a catalyst, comprising:
reacting the ethane or the ethane-containing raw gas in the presence of a catalyst,
wherein the catalyst is formed such that metallosilicate carries one of molybdenum, rhenium and tungsten, and one of rhodium and platinum as a secondary metal in addition to molybdenum, rhenium and tungsten, and
wherein the metallosilicate is formed of H-type ZSM-5 or H-type MCM-22, with the proviso that the metallosilicate is not modified with gallium.

2. A process for producing an aromatic compound, as claimed in claim 1, wherein a reaction temperature applied in a reaction made in the presence of the catalyst is from 550 to less than 750° C.

3. A process for producing an aromatic compound, as claimed in claim 1, wherein hydrogen is added to the raw gas in an amount more than 2% and less than 10%.

4. A process for producing an aromatic compound by reacting an ethane-containing raw gas in presence of a catalyst, as claimed in claim 1 further comprising the steps of
   a first stage for reforming ethane contained in the raw gas by the process for producing an aromatic compound, the process as claimed in claim 1; and
   a second stage for reacting a gas produced at the first stage in presence of a catalyst again,
   wherein the catalyst used in the second stage is formed carrying molybdenum and a platinum-group element.

5. A process for producing an aromatic compound, as claimed in claim 4, wherein the platinum-group element contained in the catalyst is rhodium, ruthenium, iridium, palladium or platinum.

6. A process for producing an aromatic compound, as claimed in claim 4, wherein hydrogen is added to the gas produced at the first stage in a reaction made by the second stage, in an amount more than 2% and less than 10%.

7. A process for producing an aromatic compound by reacting an ethane-containing raw gas in presence of a catalyst, as claimed in claim 4,
   wherein an outlet gas that has underwent the reaction made in the second stage of the process for producing an aromatic compound as claimed in claim 5 is supplied to the first stage again, thereby being circulated between the first stage and the second stage twice or more to be reacted.

8. The process for producing an aromatic compound, as claimed in claim 2, wherein a reaction temperature applied in a reaction made in the presence of the catalyst is not less than 600° C. and not more than 680° C.

9. The process for producing an aromatic compound, as claimed in claim 3, wherein hydrogen is added to the raw gas in an amount ranging from 4 to 8%.

10. The process for producing an aromatic compound, as claimed in claim 6, wherein hydrogen is added to the gas produced at the first stage in a reaction made by the second stage, in an amount ranging from 4 to 8%.

* * * * *